(12) United States Patent
Beamer (10) Patent No.: US 11,173,373 B2
(45) Date of Patent: Nov. 16, 2021

(54) ATHLETIC MONITORING GARMENT WITH NON-TRANSMITTING, NON-RECEIVING SENSOR SYSTEMS AND METHODS

(71) Applicant: adidas AG, Herzogenaurach (DE)

(72) Inventor: Bryce Beamer, Herzogenaurach (DE)

(73) Assignee: adidas AG, Herzogenaurach (DE)

( * ) Notice: Subject to any disclaimer, the term of this patent is extended or adjusted under 35 U.S.C. 154(b) by 247 days.

(21) Appl. No.: 15/862,299

(22) Filed: Jan. 4, 2018

(65) Prior Publication Data

US 2019/0201772 A1 Jul. 4, 2019

(51) Int. Cl.

| | |
|---|---|
| *A63B 71/06* | (2006.01) |
| *A41C 3/00* | (2006.01) |
| *A41D 1/00* | (2018.01) |
| *A61B 5/00* | (2006.01) |
| *A61B 5/08* | (2006.01) |
| *A61B 5/113* | (2006.01) |

(52) U.S. Cl.
CPC ........ *A63B 71/0619* (2013.01); *A41C 3/0057* (2013.01); *A41D 1/002* (2013.01); *A61B 5/08* (2013.01); *A61B 5/1135* (2013.01); *A61B 5/6804* (2013.01); *A61B 5/6823* (2013.01); *A61B 5/7455* (2013.01); *A41D 2600/10* (2013.01); *A61B 2503/10* (2013.01); *A61B 2562/164* (2013.01); *A63B 2071/0655* (2013.01); *A63B 2225/50* (2013.01); *A63B 2230/425* (2013.01)

(58) Field of Classification Search
CPC ........ A63B 71/0619; A63B 2071/0655; A63B 2225/50; A63B 2230/425; A41C 3/0057; A41D 1/002; A41D 2600/10; A61B 5/08; A61B 5/1135; A61B 5/6804; A61B 5/6823; A61B 5/7455; A61B 2503/10; A61B 2562/164
See application file for complete search history.

(56) References Cited

U.S. PATENT DOCUMENTS

| | | | | |
|---|---|---|---|---|
| 9,462,975 | B2 * | 10/2016 | Sackner | A61B 5/002 |
| 9,492,084 | B2 * | 11/2016 | Behar | A61B 5/4866 |
| 9,814,937 | B2 * | 11/2017 | Werner | A63B 24/0021 |
| 9,833,184 | B2 * | 12/2017 | Derchak | G16H 50/20 |

(Continued)

*Primary Examiner* — Malina D. Blaise
(74) *Attorney, Agent, or Firm* — Sterne, Kessler, Goldstein & Fox P.L.L.C.

(57) ABSTRACT

A garment including a breath sensor module. The breath sensor module includes a stretchable sensor configured to respond to at least one of expansion and contraction of a torso of an individual wearing the garment. The breath sensor module also may include an electronics module. The electronics module includes, for example, a processor and a haptic feedback device. In response to the processor determining that the individual's breathing meets predetermined criteria based on the response of the stretchable sensor, the haptic feedback device produces haptic feedback such that the individual is reminded to breathe. Further, the breath sensor module does not include a transmitter or a receiver configured to transmit or receive data outside of the breath sensor module. Advantageously, this allows for streamlined use, and less-intrusive reminders to the individual wearing the garment, without the complexities of signal transmission or receiving.

20 Claims, 9 Drawing Sheets

(56) References Cited

U.S. PATENT DOCUMENTS

| | | | |
|---|---|---|---|
| 2007/0043302 A1* | 2/2007 | Masuo | A61B 5/0537 600/547 |
| 2008/0000304 A1* | 1/2008 | Nagle | A61B 5/6831 73/780 |
| 2013/0123570 A1* | 5/2013 | Ly | A61M 21/02 600/27 |
| 2015/0282724 A1* | 10/2015 | McDuff | A61B 5/02427 600/479 |
| 2015/0342518 A1* | 12/2015 | Persidsky | A61B 5/6831 600/534 |
| 2016/0052131 A1* | 2/2016 | Lessing | B25J 9/142 361/679.01 |
| 2016/0089089 A1* | 3/2016 | Kakkar | A61B 5/746 600/484 |
| 2017/0209115 A1* | 7/2017 | Lonnroth | A61B 5/029 |
| 2017/0325524 A1* | 11/2017 | Hyde | A61G 7/1051 |
| 2018/0087984 A1* | 3/2018 | Hagelin | G01L 5/16 |
| 2018/0184735 A1* | 7/2018 | Longinotti-Buitoni | A61B 5/6843 |
| 2019/0336038 A1* | 11/2019 | Gorgutsa | A61B 5/6804 |

* cited by examiner

ATHLETIC MONITORING GARMENT WITH NON-TRANSMITTING, NON-RECEIVING SENSOR SYSTEMS AND METHODS

FIELD OF THE INVENTION

Embodiments of the present invention generally relate to streamlined athletic monitoring garments having breath sensor modules, including flexible sensor systems, such as printed capacitive sensor systems used in substrate applications. Haptic feedback is provided to the user, without complicated user-interfaces or other connected devices.

BACKGROUND OF THE INVENTION

Athletic activity is important to maintaining a healthy lifestyle and is a source of entertainment for many people. In recent years athletes have employed additional tools in an effort to assist in tracking and coaching workouts. For example, GPS and accelerometer based devices may be used to provide speed and distance information when running. Fitness monitoring devices have also been developed that are capable of recording information about an individual's performance during an athletic activity using sensors, and in some cases providing feedback about the individual's performance. Some fitness monitoring devices employ sensors attached to the individual's body, while other fitness monitoring devices rely on sensors attached to a piece of athletic equipment. Such sensors may be capable of measuring various physical and/or physiological parameters associated with the individual's physical activity.

But with respect to providing this information, existing athletic/fitness activity monitoring, training, and coaching systems suffer from a number of drawbacks. Many existing systems are limited in the amount of feedback or coaching that they can give, and may be bulky, heavy, and not integrated into a piece of equipment. For example, many systems require a separate piece of equipment, such as a smart phone, smart watch, other stand-alone wearable device, or the like. These systems are not suitable for monitoring in many real world athletic competitive or training sessions.

Additionally, many current devices require a high level of user input or engagement, which may detract from an easy transition to and maintaining use of a monitoring garment. Further, many current devices do not auto-detect activity; that is, a user must "tell" the device that they are starting an activity they would like to monitor. Further, for some activity, such as yoga, the feedback may be distracting or not provided in a convenient manner (e.g., having to pull up a smartphone screen during yoga practice). Individualized activity, particularly that which relies on mental awareness and focus, such as yoga, will benefit from the systems and methods described below.

Additionally, existing garment sensors may measure strain, displacement, and the like but also suffer from several drawbacks. In the case of stretchable garment sensors, e.g., sensors printed using conductive ink, cracks or fissures may develop in one or more of the sensor layers. Cracks may reduce accuracy of the sensor signal, or destroy the signal completely.

BRIEF SUMMARY OF THE INVENTION

What is needed are athletic activity training, and coaching, systems and methods having improved capabilities over existing systems, thus offering individuals engaged in athletic activities and other interested observers better tools to improve their performance through feedback. In this regard, sensors integrated within garments offer an advantage, especially with regard to base layers of clothing worn close to the skin, by providing properly fitting garments that move with the body, allowing sensors to collect accurate and precise data, without being overly intrusive or distracting. Also needed are improvements in layering and printing sensors, in particular capacitive sensors. Strain relief systems in printed sensor systems, particularly capacitive sensor systems are also required.

At least some of the embodiments of the present invention satisfy the above needs and provide further related advantages as will be made apparent by the description that follows.

Some embodiments are directed to a garment including a breath sensor module. The breath sensor module includes a stretchable sensor configured to respond to at least one of expansion and contraction of a torso of an individual wearing the garment. The breath sensor module also may include an electronics module. The electronics module includes, for example, a processor and a haptic feedback device. In response to the processor determining that the individual's breathing meets predetermined criteria based on the response of the stretchable sensor, the haptic feedback device produces haptic feedback such that the individual is reminded to breathe. Further, the breath sensor module does not include a transmitter or a receiver configured to transmit or receive data outside of the breath sensor module. Advantageously, this allows for streamlined manufacturing and use, and less-intrusive reminders to the individual wearing the garment, without the complexities of signal transmission or receiving.

In some embodiments, the predetermined criteria consists of a determination that the individual has not taken a breath within a pre-defined time threshold. In some embodiments, the predetermined criteria consists of a determination that the individual is not breathing in a regular pattern. The haptic feedback is a vibration pattern in some embodiments. Further, the electronics module is separable from the breath sensor module. In this regard, ability to launder the garment is improved, and more flexible charging of the electronics module is possible (i.e., the individual may continue wearing the garment while the electronics module is charging).

The electronics module may include a switch operable by the individual to begin monitoring of the breath by the stretchable sensor. For example, it may be a toggle switch or other suitable switch, or the stretch sensor module may also be configured as an input, e.g., the individual may tap a pattern or press on the sensor for a predetermined amount of time.

In some embodiments, the stretchable sensor is a capacitive sensor. As described herein, the stretchable sensor (e.g., capacitive sensor) may include a stretchable substrate, a first conductor assembly disposed on the substrate, and a second conductor assembly disposed on the substrate and positioned above the first conductor assembly such that the second conductor assembly overlaps the first conductor assembly. Advantageously, a connection between the stretchable sensor and the electronics module includes a strain relief member configured to isolate the stretchable sensor such that it measures only the stretching of the sensor in a direction configured to measure the breathing of the individual. This helps to aid in removing concern about motion artifacts, e.g., the requirement for compensation due to difference in individual posture, for example when in different yoga poses.

In some embodiments, the wherein the breath sensor module does not include an audible output or visual output configured to provide feedback to remind the individual to breathe.

The garment includes a band of elastic material configured to encircle the torso of the individual when the garment is worn by the individual—the stretchable sensor extends longitudinally along the band. The electronics module is encapsulated in fabric of the garment such that it is not visible from the exterior of the garment when the individual is wearing it, in some embodiments. This also provides an aesthetic appeal of the garment, camouflaging the electronics so as not to detract from the appearance of the garment.

Some embodiments are directed to a method for providing feedback about respiratory activity to an individual wearing a garment (e.g., garment with a breath sensor module). The method includes sensing an event indicating a start of monitoring of the individual's respiratory activity, monitoring the individual's respiratory activity, and determining that the individual's breathing meets predetermined criteria based on the monitoring. In sensing of the event, the user input required to begin monitoring of the activity is minimized, in some instances to zero user input required. In some embodiments, the event sensed comprises one of a user input, determining that the user is breathing, and detection of the garment being worn. In response to determining that a pre-defined respiratory event occurred, the method further includes providing immediate feedback to the user through the breath sensor module. The breath sensor module does not include a transmitter or a receiver configured to transmit or receive data outside of the breath sensor module, in some embodiments. In some embodiments, the predetermined criteria consists of a determination that the individual has not taken a breath within a pre-defined time threshold. In some embodiments, the criteria is that the individual is breathing in an irregular pattern. In some embodiments, the immediate feedback is haptic feedback in the form of a vibration pattern.

In some embodiments, the method includes receiving a user input indicating a finish of monitoring of the individual's respiratory activity. The electronics module is separable from the breath sensor module, in some embodiments. In some embodiments, the garment comprises an athletic bra, and the electronics module is encapsulated in the fabric of the garment such that it is not visible from an exterior of the garment when the individual is wearing it.

Some embodiments are directed to a respiration monitoring system. In some embodiments, the system includes a garment configured to be worn by an individual, a stretchable sensor attached to the garment, a processor operatively coupled to the sensor; and a breath sensor module operatively coupled to the processor. The stretchable sensor is configured to transmit a non-transitory respiration activity signal to the processor, and in response to the respiration activity signal the processor determines that a predetermined criteria is met. Further, in response to determining that the predetermined criteria is met, the processor causes the breath sensor module to provide immediate haptic feedback to the individual wearing the garment.

Advantageously, and distinct from conventional approaches, these features contribute to a reduced cost of manufacture, and easier manufacturing/assembly of a finished garment. Further, without complex electronics and transmission, there is a marked power consumption compared to conventional monitoring garments.

Additional features of embodiments of the invention will be set forth in the description that follows, and in part will be apparent from the description, or may be learned by practice of the invention. Both the foregoing general description and the following detailed description are exemplary and explanatory and are intended to provide further explanation of the invention as claimed.

BRIEF DESCRIPTION OF THE DRAWINGS/FIGURES

The accompanying figures, which are incorporated herein, form part of the specification and illustrate embodiments of the present invention. Together with the description, the figures further serve to explain the principles of and to enable a person skilled in the relevant arts to make and use the invention.

DETAILED DESCRIPTION OF THE INVENTION

The present invention will now be described in detail with reference to embodiments thereof as illustrated in the accompanying drawings.

The methods and systems discussed above are further described below. The figures below may apply to both the method and system embodiments of the invention. While capacitive sensor systems are described, the various methods and systems described herein may be applied to other types of sensor systems, for example, resistive, inductive, etc.

Figure 1A:
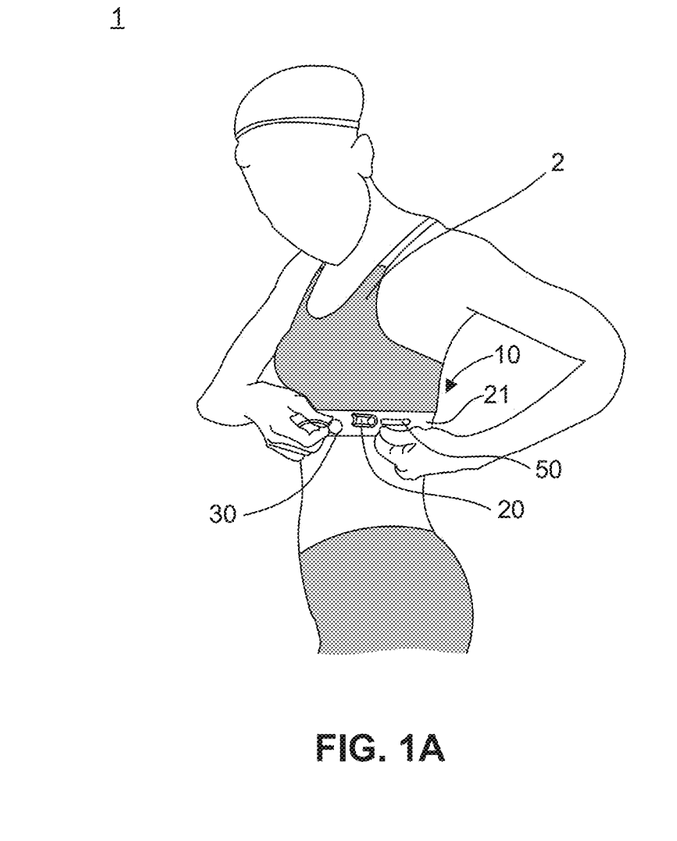
FIGS. 1A and 1B are illustrations of an individual using a garment including a breath sensor module according to an embodiment of the present invention.
Figure 1B:
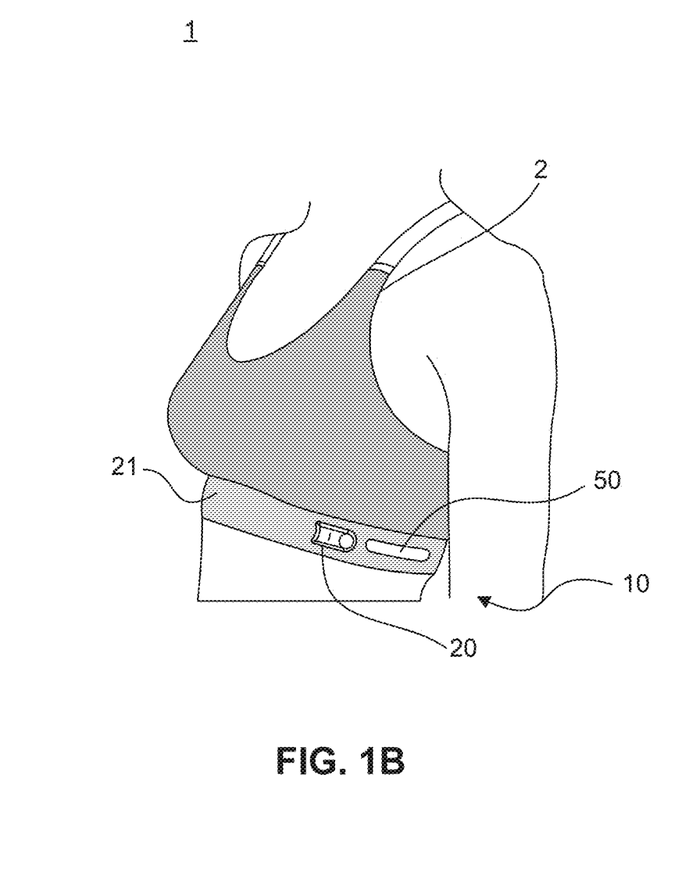

Turning to FIGS. 1A and 1B, individual 1 is shown using a garment 2, particularly a sports bra, with breath sensor module 10, including electronic module 20 and stretchable sensor 100. As shown in FIG. 1A, the breath sensor module 10 or electronic module 20 may be coupled to data or charging system 30, for example, to download sensor data or charge the electronic module. In use, however, data or charging system 30 may be wireless such that individual 1 is free to move without the need for extra components, such as wires or cable connections. Moreover, is some embodiments, charging system 30 is standalone, and the breath sensor module 10 does not include a transmitter or a receiver configured to transmit or receive data outside of the breath sensor module. Additionally, breath sensor module 10 and electronic module 20 may not include a battery, and instead simply use a capacitive sensor system as described herein as energy storage, recharging through inductive or capacitive charging. In this way, there may be a high charging rate, e.g. approximately a 15 second charge provides approximately 3-4 hours of use.

As described generally above, the garments described herein overcome many prior challenges with designing effective but unobtrusive monitoring garments. What is needed are athletic activity training, and coaching, systems and methods having improved capabilities over existing systems, thus offering individuals engaged in athletic activities and other interested observers better tools to improve their performance through feedback. In this regard, sensors such as breath sensor module 10, integrated within garments, offer an advantage, especially with regard to base layers of clothing worn close to the skin, by providing properly fitting garments that move with the body, allowing sensors to collect accurate and precise data, without being overly intrusive or distracting.

For example, during yoga practice, mindfulness of breath is particularly important to individuals engaged in the activity. Individual's breathing impacts their performance biometrics, and can affect their performance in the activity. Additionally, breath control is one of the pieces of an activity that an individual can most easily control, but it is difficult to obtain instruction on, especially if an individual is engaged in a group activity or class, such as a yoga class. An instructor is unable to tell if an individual is breathing, or inhaling at the right time, consistently, or in a regular pattern. It is difficult to determine that an individual is holding their breath, and remind them to breathe. In this regard, breath sensor module 10 may operate to remind the individual to breathe if the individual has stopped to breathe, or identify irregular breathing patterns such that it reminds the individual to normalize or regulate their breathing. This is especially true with activities that require a great deal of focus, such as challenging yoga poses.

Indeed, breath sensor module 10 may be completely local, such that it does not require a phone, smart watch, or any additional external device to operate during use to distract the individual further from their activity. In this way, breath sensor module 10 allows the individual to maintain focus and engagement on the activity, while being provided with a gentle reminder to be cognizant of breathing regularly, even during challenging activity. To be sure, the embodiments described herein may not provide a suggested rhythm, or pattern, such as a metronome. Rather, the breath sensor module 10 is generally only designed to provide reminders to breathe if an individual has not taken a breath after a certain period of time, or if the breath sensor module 10 recognizes an abnormal breathing pattern. This is a less intrusive way to remind an individual to breathe.

With this background, as described above, FIG. 1 shows garment 2 including a breath sensor module 10. Garment 2 is configured as an athletic bra, in some embodiments. Other forms or variations of garment 2 are contemplated, such that a breath sensor module 10 may monitor an individual's breath.

As shown in the FIGS., breath sensor module 10 includes a stretchable sensor 50 configured to respond to at least one of expansion and contraction of a torso of an individual wearing garment 2. The breath sensor module 10 also may include an electronics module 20, which includes, for example, a processor and a haptic feedback device. In response to the processor determining that the individual's breathing meets predetermined criteria based on the response of stretchable sensor 50, the haptic feedback device produces haptic feedback such that the individual is reminded to breathe. In this way, the individual may continue focus on the activity at hand, e.g., yoga practice. Further, in one embodiment, the breath sensor module 10 does not include a transmitter or a receiver configured to transmit or receive data outside of breath sensor module 10. As discussed above, this allows for streamlined design and use, and less-intrusive reminders to the individual wearing garment 2, without the complexities of signal transmission or receiving. In this embodiment, no smartphone, smart watch, screen notification, etc. is required, and therefore distractions to the individual are minimized, allowing them to focus their effort on the athletic task at hand. However, in other embodiments, the breath sensor module may be capable operating in two different modes: one mode without the support of an additional external device, and one mode with the support of an additional external device. These embodiments give the user the option of enabling or disabling the ability to connect with these external devices.

In some embodiments, the predetermined criteria consists of a determination that the individual has not taken a breath within a pre-defined time threshold. In some embodiments, the predetermined criteria consists of a determination that the individual is not breathing in a regular pattern. The haptic feedback is a vibration pattern in some embodiments. The haptic feedback may include auditory feedback, subtle such that the individual is the only one to hear it. In some embodiments, the wherein the breath sensor module does not include an audible output or visual output configured to provide feedback to remind the individual to breathe. Further, the electronics module 20 is separable from the breath sensor module 10. In this regard, ability to launder garment 2 is improved, and more flexible charging of the electronics module 20 is possible (i.e., the individual may continue wearing the garment while electronics 20 module is charging). In some embodiments, the haptic feedback may progressively intensify, if the individual's breathing does not resume a regular pattern, or if the individual continues to not take a breath. This feature may aid in breaking the individual's concentration in order to sufficiently remind them to breath, with the haptic feedback resuming a normal intensity on a subsequent event. In this way, garment 2 coupled with breath sensor module 10 strikes a balance between unintrusive feedback and effectiveness at gaining an individual's attention to remind them to breathe.

The electronics module 20 may include a switch operable by the individual to begin monitoring of the breath by the stretchable sensor 50. For example, it may be a toggle switch, or the breath sensor module 10 may also be configured as an input, e.g., the individual may tap a pattern or press on the sensor itself for a predetermined amount of time. Electronics module 20 may be programmed to recognize these patterns or duration as commands to begin monitoring, start monitoring, change feedback intensity, etc. In some embodiments, automatic detection of an individual wearing the garment 2 is what will indicate to the electronics module 20 to begin monitoring of the breath by the stretchable sensor 50. The user interface of breath sensor module 10 is thus intuitive, without complex pairing between multiple devices, user accounts, servers, etc. The garment 2 thus provides a personalized, private experience to the individual, without a complex interface.

The garment 2 includes a band of elastic material 21 configured to encircle the torso of the individual when garment 2 is worn by the individual. As configured, stretchable sensor 50 then extends longitudinally along the band, which aids in detecting the expansion or contraction (or both of the individual's torso). In some embodiments, breath sensor module 10 detects the change point from inhaling to exhaling, or vice versa. In this way, auto detection is possible, that is, the individual does not have to "tell" the garment to begin monitoring. The electronics module 20 is encapsulated in fabric of garment 2 in some embodiments. It may be stitched directly into garment 2, or may be encapsulated in a pocket, for example. In this way, electronics module 20 is not visible from the exterior of the garment when the individual is wearing it, in some embodiments. This also provides an aesthetic appeal of the garment, camouflaging the electronics so as not to detract from the appearance of the garment.

Some embodiments are directed to a respiration monitoring system, including garment 2 and stretchable sensor 50. The stretchable sensor 50 is attached to garment 20. Additionally, a processor is operatively coupled to the sensor; and a breath sensor module 10 is operatively coupled to the processor. The stretchable sensor 50 is configured to transmit a non-transitory respiration activity signal to the processor, and in response to the respiration activity signal the processor determines that a predetermined criteria is met. Further, in response to determining that the predetermined criteria is met, the processor causes the breath sensor module to provide immediate haptic feedback to the individual wearing the garment. In streamlining this construction, and distinct from conventional approaches, these features contribute to a reduced cost of manufacture, and easier manufacturing/assembly of a finished garment. Further, without complex electronics and transmission, there is a marked power consumption compared to conventional monitoring garments.

Figure 9:
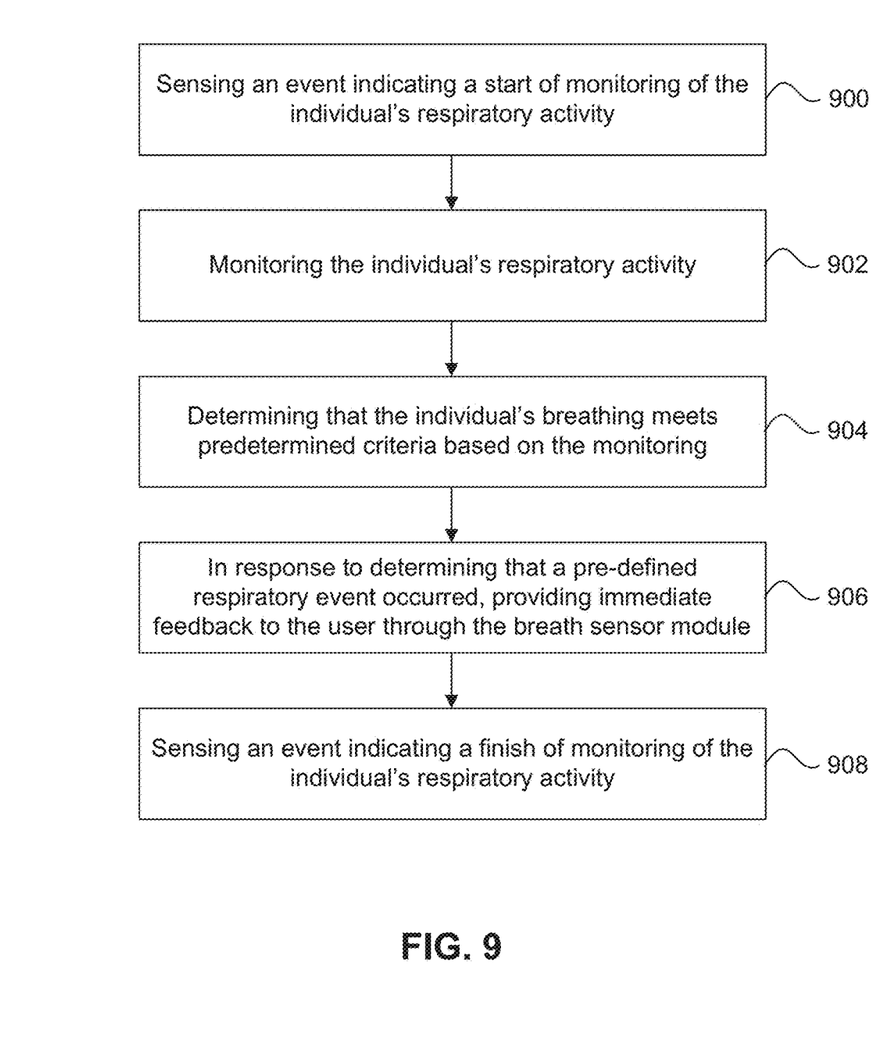
FIG. 9 shows a flowchart of a method for providing feedback about respiratory activity to an individual wearing a garment with a breath sensor module.

Some embodiments are directed to a method for providing feedback about respiratory activity to an individual wearing a garment (e.g., garment with a breath sensor module). Such a method is illustrated in FIG. 9, for example, starting with operation 900. At operation 900, the method includes sensing an event indicating a start of monitoring of the individual's respiratory activity. At operation 902, the method includes monitoring the individual's respiratory activity, and at operation 904, the method includes determining that the individual's breathing meets predetermined criteria based on the monitoring. In response to determining that a pre-defined respiratory event occurred, the method further includes (at operation 906, providing immediate feedback to the user through the breath sensor module. As above, the breath sensor module does not include a transmitter or a receiver configured to transmit or receive data outside of the breath sensor module, in some embodiments. In some embodiments, the predetermined criteria consists of a determination that the individual has not taken a breath within a pre-defined time threshold. In some embodiments, the event sensed comprises one of a user input, determining that the user is breathing, and detection of the garment being worn. In some embodiments, the immediate feedback is haptic feedback in the form of a vibration pattern. In some embodiments, the method includes operation 908, sensing an event indicating a finish of monitoring of the individual's respiratory activity (e.g., receiving a user input indicating a finish of monitoring of the individual's respiratory activity, detecting that the garment is no longer being worn, etc.). The electronics module is separable from the breath sensor module, in some embodiments. In some embodiments, the garment comprises an athletic bra, and the electronics module is encapsulated in the fabric of the garment such that it is not visible from an exterior of the garment when the individual is wearing it.

Strain sensors in general are used to measure strain on an object. In some instances, a common type of strain gauge consists of an insulating flexible backing which supports a metallic foil pattern. The gauge is attached to the object by a suitable adhesive. As the object is deformed, the foil is also deformed, causing its electrical resistance to change. This resistance change, usually measured using a Wheatstone bridge, is related to the strain by the quantity known as the gauge factor.

Capacitance is the ability of a system to store an electric charge, that is, the ratio of the charge in a system to the corresponding change in its electric potential. Further, in the case of a parallel plate capacitor, capacitance is directly proportional to the surface area of the conductor plates and inversely proportional to the separation distance between the plates. That is, if the area of the conductor plates are increased, a capacitance measurement increases. Similarly, if the separation distance between the plates is decreased, a capacitance measurement increases. Other configurations of capacitive sensors rely on capacitance changing based on particular geometrical relations between components changing. Thus, certain dimensional relationships between components may be applied as above to correlate change in capacitance with a change in strain. This is in contrast to resistive-strain sensor applications. Compared to capacitive applications, resistance based sensors generally suffer from high levels of hysteresis and high levels of signal noise.

As further described below, in some embodiments, the stretchable sensor 50 is a capacitive sensor. As described herein, the stretchable sensor 50 (e.g., capacitive sensor) may include a stretchable substrate, a first conductor assembly disposed on the substrate, and a second conductor assembly disposed on the substrate and positioned above the first conductor assembly such that the second conductor assembly overlaps the first conductor assembly. Advantageously, a connection between the stretchable sensor and the electronics module includes a strain relief member configured to isolate the stretchable sensor such that it measures only the stretching of the sensor in a direction configured to measure the breathing of the individual. This helps to aid in removing concern about motion artifacts, e.g., the requirement for compensation due to difference in individual posture, for example when in different yoga poses.

The repeated stresses on stretchable sensor 50, coupled with the need for a robust garment that can withstand repeated laundering, benefits from improvements related to stretchable sensors in general. Several such improvements are now described with reference to the figures.

Figure 2:
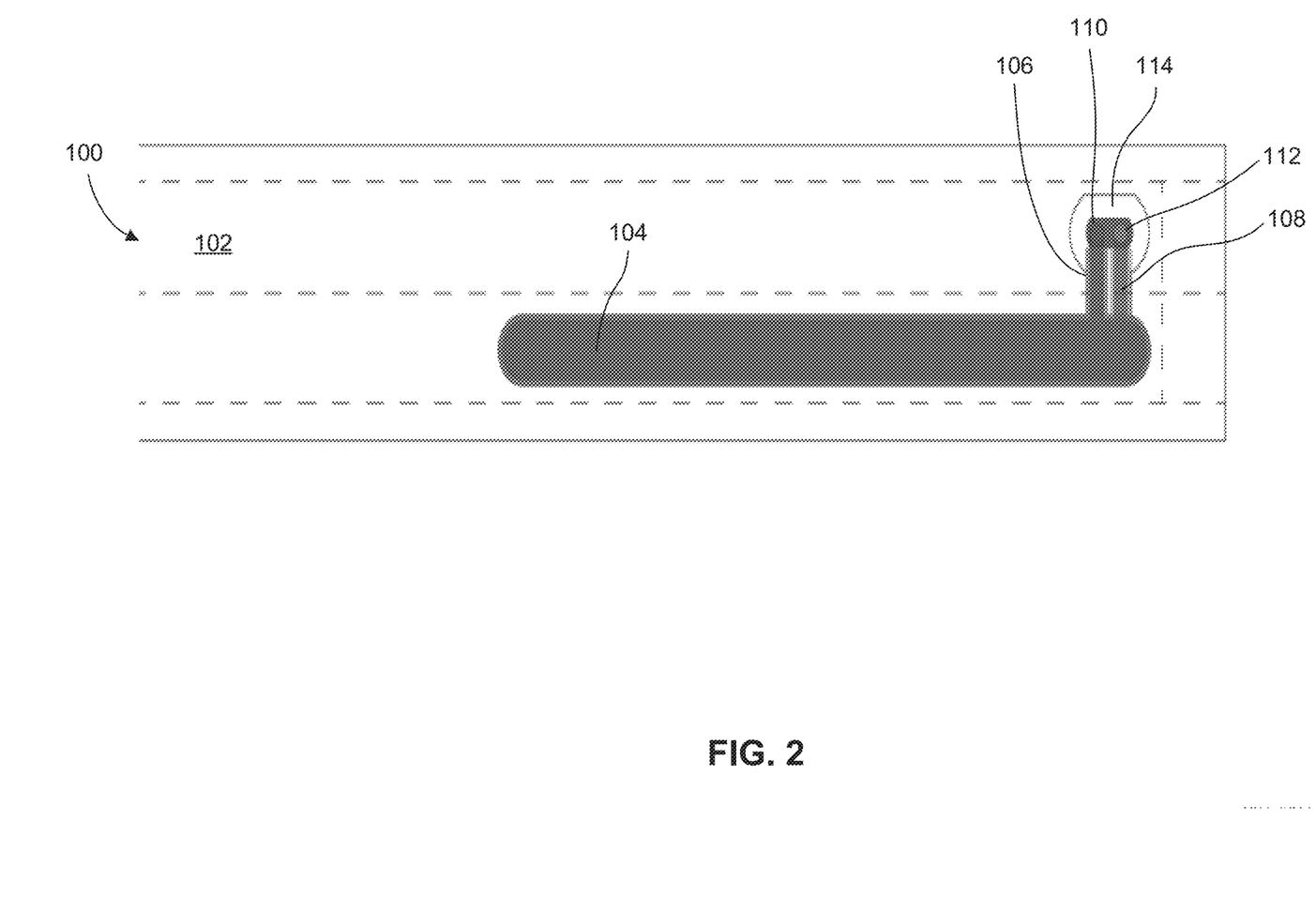
FIG. 2 is an illustration of a capacitive sensor system according to embodiments of the present invention.

As shown in FIG. 2, stretchable sensor 50 employed by breath sensor module 10 may include a stretchable sensor such as capacitive sensor system 100, including a substrate, e.g., stretchable substrate 102. As shown, substrate 102 may be operatively coupled with capacitive area 104, formed for example with conductive ink. As described below, with reference to FIG. 5, capacitive sensor systems disclosed may include at least two conductor assemblies, for example, conductor assembly 500 and conductor assembly 600, disposed below conductor assembly 500, which define capacitive area 104. Further detail of the construction and layering of the conductor assemblies into a finished capacitive sensor system, including substrate structure is provided below, with reference to FIG. 5.

Capacitive area 104 may extend along a stretching direction of substrate 102, such that when an individual moves along the stretching direction, the area of capacitive area 104 changes, which results in a change in capacitance. As shown, in some embodiments, capacitive sensor system 100 includes leads 106/108 that are screen printed in the same way as capacitive area 104, and extend substantially perpendicular to capacitive area 104. Leads 106/108 may include terminal ends 110/112, that connect to connection pad 114, such that the electrical signal (e.g., change in capacitance that may be converted to a strain measurement) from the sensor may be transmitted through the system to, for example, an electronic module (not shown).

As above, capacitance in a parallel plate capacitor is calculated as the area of the capacitive plates divided by the distance between them, multiplied by a permittivity constant. In this regard, a measured capacitance change due to stretching the sensor and thus changing the capacitive area 104, for known permittivity and constant or estimated distance between layers of conductor assemblies 500/600, strain may be sensed or calculated based on the change in the capacitive area 104.

As shown in FIG. 2, during repeated use, the printed sensor layers in capacitive area 104 may develop cracks or fissures, due to repeated strain cycling, prolonged strain, or large stress magnitudes. Various factors contribute to the formation of cracks or fissures, including direction of strain, material or manufacturing variation, number of cycles, length of strain, types of or magnitudes of stress, etc. This decreases the effective capacitive area 104 as the circuit becomes incomplete, and may reduce accuracy of the sensor or destroy the sensor completely, as it cuts off a large amount of capacitive area 104 from the ultimate sensor circuit.

Figure 3:
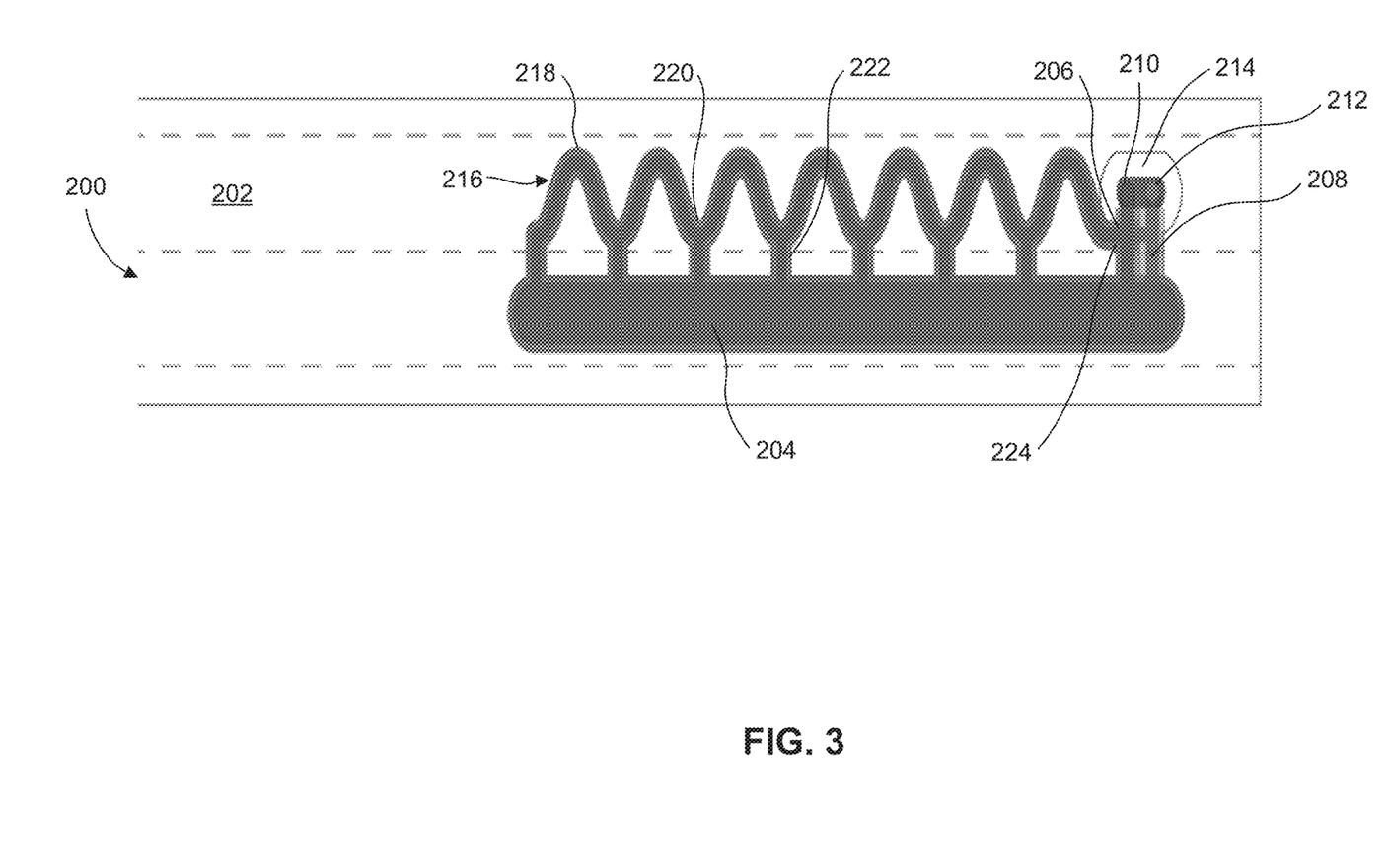
FIG. 3 an illustration of a capacitive sensor system according to embodiments of the present invention.

As shown in FIG. 3, in some embodiments, capacitive sensor 200 includes many of the same components as capacitive sensor system 100, such as substrate 202, capacitive area 204, leads 206/208 that extend substantially perpendicular to capacitive area 204. Leads 206/208 may include terminal ends 210/212 that connect to connection pad 214. Additionally, in some embodiments, capacitive sensor 200 includes redundancy member 216. Redundancy member 216 may include generally serpentine peaks 218 and troughs 220, and may be printed in the same manner as capacitive area 204. Redundancy member 216 and capacitive area 204 are operatively and structurally coupled at junctions 222. In some embodiments, redundancy member 216 may be operatively and structurally coupled to one or more of the conductor assemblies 500/600, at junctions 222. Redundancy member 216 may include lead 224 that connects to lead 206 or 208, for example. In some embodiments, redundancy member 216 connects directly to connection pad 214.

In some embodiments the first and second leads 206/208 may extend substantially parallel to one another. In some embodiments, first and second leads 206/208 may extend such that they do not overlap one another, in contrast to the capacitive area 204, where conductor assemblies 500/600 may overlap one another.

In some embodiments, redundancy member 216 is configured to absorb stress in the stretching direction. As shown, even if capacitive sensor 200 develops cracks or fissures through capacitive area 204 through repetitive strain cycling, the connection to the overall circuit is not completely disrupted because the capacitive area is still coupled via redundancy member 216 at junctions 222. Advantageously, the generally serpentine structure including peaks 218 and troughs 220 lend greater flexibility to the printed layers, and resist the development of cracks and fissures over repeated strain cycling. In some embodiments, the curved nature of the generally serpentine structure induces bending/buckling out of plane relative to the general plane of the sensor, which increases strain relief and avoids formation of fissures or cracks due to material fatigue from either strain cycling or large stress magnitudes. In some embodiments the conductor assemblies 500/600 have a longitudinal configuration extending in a stretching direction. In some embodiments, redundancy member 216 has a serpentine configuration, including at least a serpentine peak and a serpentine trough. In some embodiments, redundancy member 216 is coupled to the one of the conductor assemblies 500/600 via junction 222 coupled to the serpentine trough.

As used herein, "serpentine" includes waveform patterns of constant or variable amplitudes, generally sinusoidal patterns, curvilinear forms, "horseshoe" type waveforms where the peaks and troughs are nested next to one another, etc.

Figure 4:
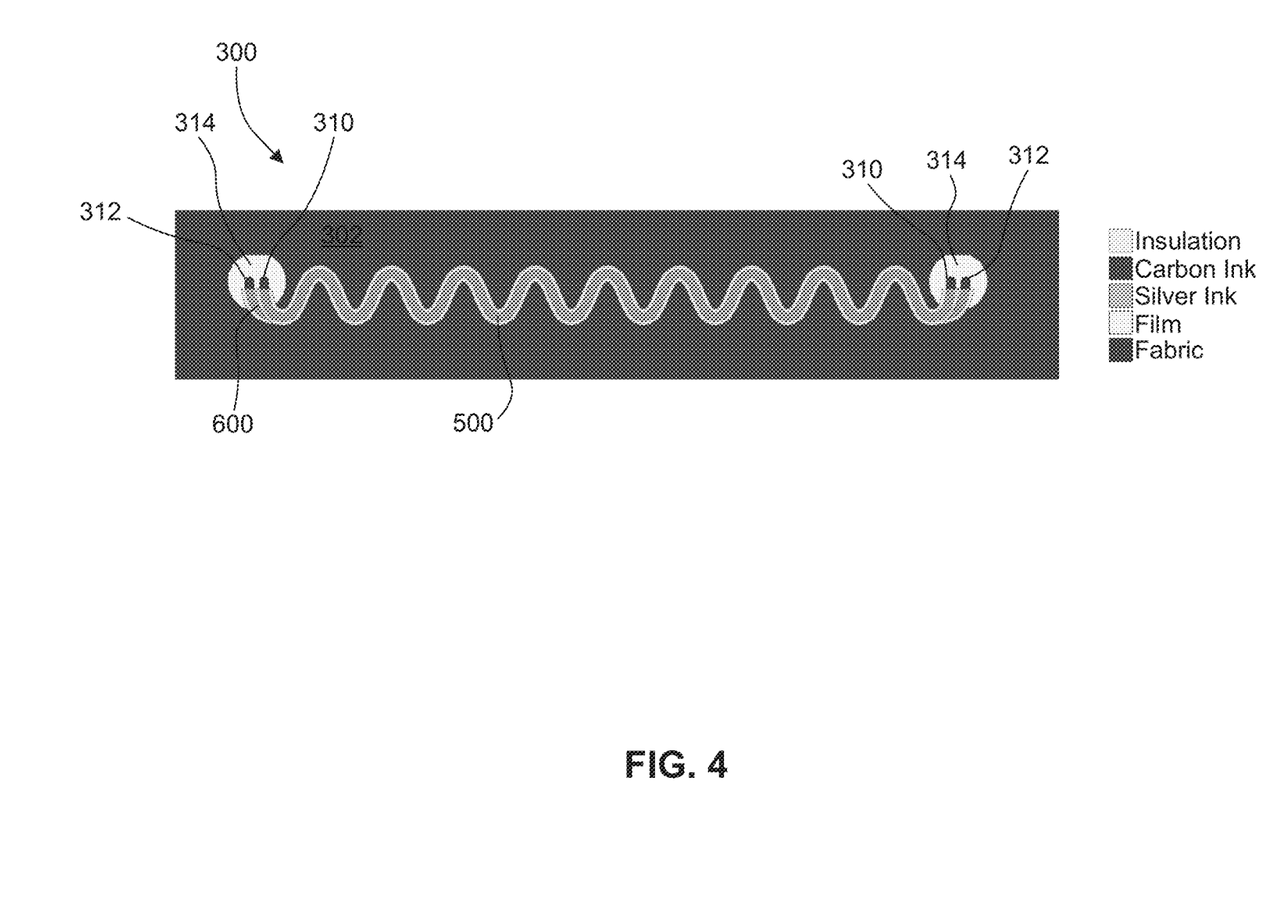
FIG. 4 is an illustration of a capacitive sensor system according to embodiments of the present invention.
Figure 5:
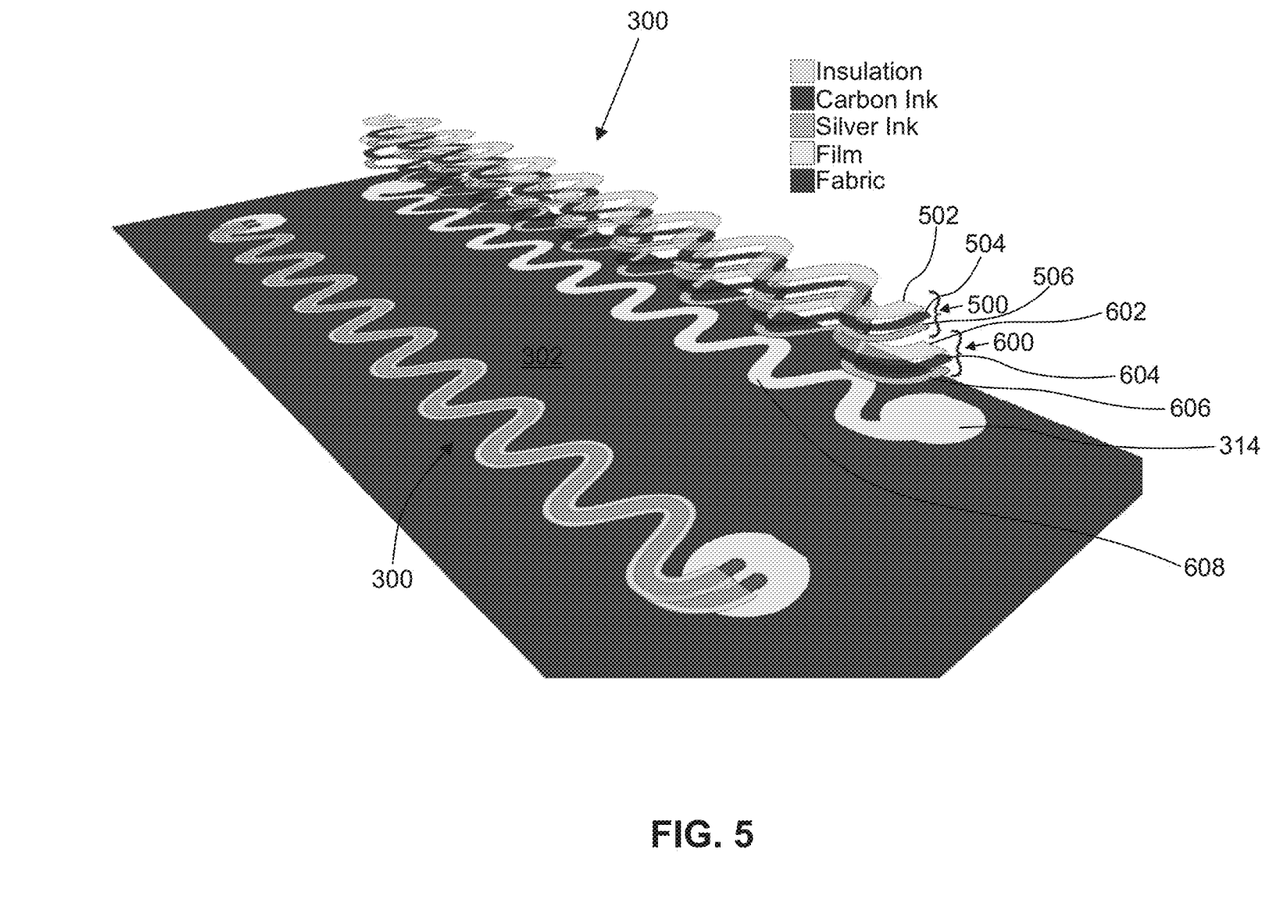
FIG. 5 is a partial exploded view of the capacitive sensor system shown in FIG. 4 according to embodiments of the present invention.

As shown in FIGS. 4 and 5, in some embodiments, first conductor assembly 600 is disposed on the substrate, and second conductor assembly 500 is disposed on the substrate and above the first conductor assembly such that the second conductor assembly generally overlaps the first conductor assembly. In some embodiments, a first lead 312 is positioned at a terminal end of the first conductor assembly 600, and a second lead 310 is positioned at a terminal end of the second conductor assembly 500 and offset from the first lead 312. In some embodiments, leads 310/312 extend substantially parallel to the one another. In some embodiments, one or more of leads 310/312 extend substantially perpendicular to one or more of the conductor assemblies. In some embodiments, the first terminal end of each of the conductor assemblies extend substantially parallel to one another. In some embodiments, the first terminal end of each of the conductor assemblies is offset from one another. In some embodiments, the second terminal end of each of the conductor assemblies extend substantially parallel to one another. In some embodiments, the second terminal end of each of the conductor assemblies is offset from one another. In some embodiments, the conductor assemblies 600/500 are used as a conductor for other sensors or actuators beyond capacitive sensors. Each of the conductive assemblies or layers as described herein may be similarly used for conducting components for other sensors or actuators beyond capacitive sensors.

As shown in FIGS. 4 and 5, in some embodiments, the capacitive area may be configured as a serpentine structure including peaks 318 and troughs 320, taking advantage of additional flexibility in configuration. As shown, in some embodiments, a first serpentine conductor assembly 600 may be disposed on the substrate and having first and second terminal ends 312 coupled to the substrate 302, a second serpentine conductor assembly 500 disposed above and overlapping the first conductor assembly 600 and having first and second terminal ends 310 coupled to the substrate, wherein a terminal end of the first conductor assembly 600 is offset from the corresponding terminal end of the second conductor assembly 500. In some embodiments, the serpentine structure may have a predetermined frequency, dimensions, pitch, etc. In some embodiments, these dimensions may vary along the length of sensor 300, or may be constant.

To illustrate the general layering structure of capacitive sensor systems 100, 200, and 300, FIG. 5 shows a partial exploded view of an exemplary layering structure according to an embodiment of various capacitive sensor systems as disclosed herein. As shown, capacitive sensor systems 100, 200, and 300 may include at least two conductor assemblies, for example, conductor assembly 500 and conductor assembly 600, disposed below conductor assembly 500. As shown, each conductor assembly may be configured with multiple layers, for example, a layer of conductive ink 606/506, such as silver ink, may be followed with an intermediate layer of conductive ink 604/504, such as carbon ink. In some embodiments, an insulation layer 602/502 may be disposed above intermediate layer 604/504. In some embodiments, the number of conductive layers, type of material, order of materials, etc., may be varied. With reference to embodiments including redundancy member 216, in some embodiments, redundancy member 216 may be formed only in some of the particular layers of conductor assemblies 500/600. In some embodiments, redundancy member 216 may include different geometries at different layers of conductor assemblies 500/600.

In some embodiments, the base layer of the conductive assembly smooths the printing surface for subsequent layers. In general, carbon layers tend to me more stable, durable, and washable, but have lower conductivity. In contrast, silver layers are less durable but offer relatively higher conductivity at the expense of increased cost. In some embodiments, layers including carbon are used to protect layers including silver, and may also lower cost. Additionally, other types of layers, such as silver-silver chloride may improve certain types of additional physiological signals, such as EMG or ECG signals. In some embodiments, insulation layers are printed to reduce the number of films needed, or to extend the performance of the films, or improve the performance of the capacitive sensor. In some embodiments, insulation is positioned between adjacent conductive layers. In some embodiments, insulation is positioned between capacitive assemblies and other capacitive or conductive bodies, (e.g., the body of a subject, a sweaty fabric).

In some embodiments, multiple layers of conductors or conductive assemblies reduce signal noise generated from the body. In some embodiments, multiple layers of conductors or conductive assemblies may be used as an input sensor, such as a touch sensor.

As shown, in some embodiments, the layers of each of the conductor assemblies may be separately printed, for example, screen printed or ink jet printed, as traces disposed on top of each other in layers, prior to integration with the garment. In some embodiments, the layers are printed (e.g., screen printed, ink-jet printed, direct deposition, stenciling, etc.) and then cut (e.g., laser cut, die cut, etc.) out to their desired shape prior to integration. In some embodiments, a film layer 608 may be used as a bottom-most layer on one or more of the conductor assemblies 500/600, acting as an effective platform for one or more of the conductor assemblies. In some embodiments, film layer 608 may be, for example a polyurethane film. In this regard, film layer 608 is configured as a stretchable layer. In some embodiments, film layer 608 may be predisposed on substrate 302. In some embodiments, film layer 608 may be applied to substrate 302 once the conductor assemblies have been printed onto it. In some embodiments, the conductor assemblies 500/600 may be stacked, and then applied to substrate 302, such as a fabric for a garment, for example, through heat pressing.

Figure 6:
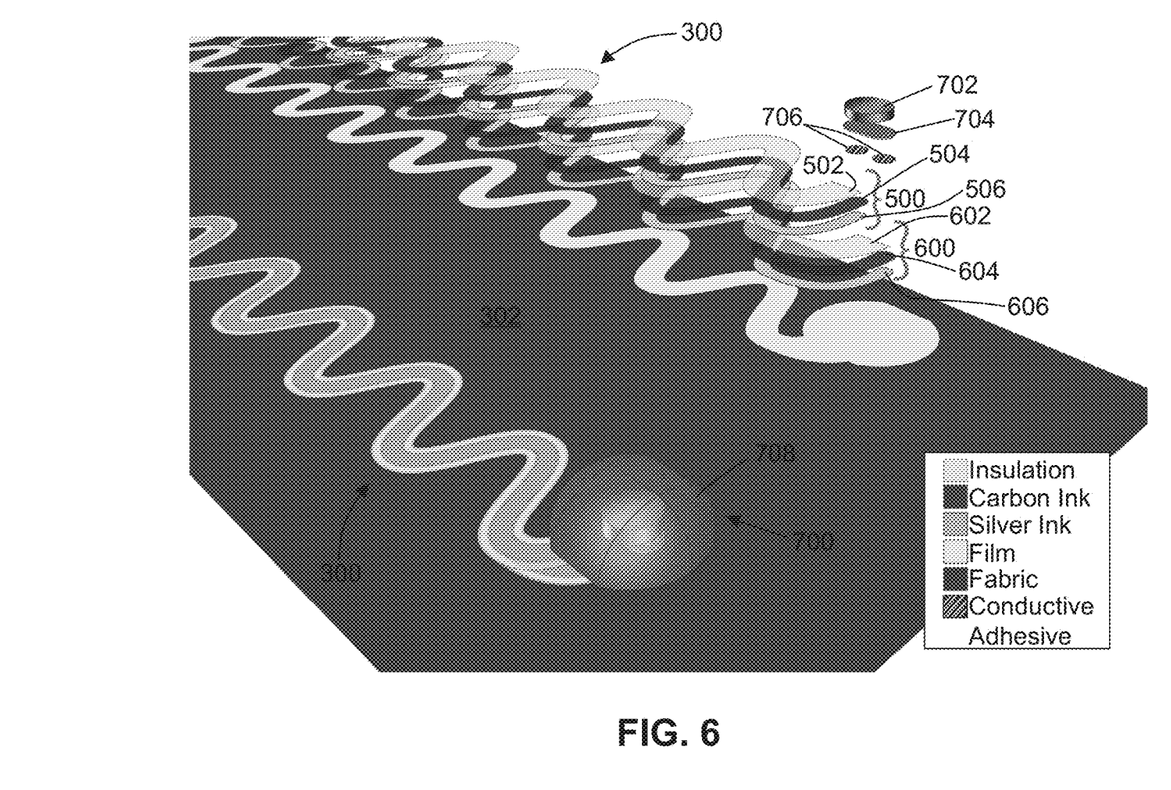
FIG. 6 is a partial exploded view of a capacitive sensor system according to embodiments of the present invention.

Turning to FIG. 6, to illustrate additional features along with general layering structure of capacitive sensor systems 100, 200, and 300, FIG. 6 shows a partial exploded view of an exemplary layering structure (similar to FIG. 5) according to an embodiment of various capacitive sensor systems as disclosed herein. As shown, capacitive sensor systems 100, 200, and 300 may include at least two conductor assemblies, for example, conductor assembly 500 and conductor assembly 600, disposed below conductor assembly 500. FIG. 6 additionally shows exemplary feedback module 700. In some embodiments, feedback module 700 includes, for example, haptic motor 702, which may provide haptic feedback to an individual. In some embodiments, a haptic circuit 704, e.g., a printed circuit board, may be operatively coupled to haptic motor 702, as well as the capacitive sensor system. This coupling occurs through connections 706, for example. Connections 706 include, for example, conductive adhesive. In some embodiments, other connection types may be used, for example, soldering, mechanical connectors, and the like. In some embodiments, feedback module 700 includes a housing 708. In some embodiments, housing 708 may be an elastomer overmolded assembly, encasing the feedback module 700. In some embodiments, housing 708 may be other materials, for example, a plastic, metal, or fabric material.

Figure 7:
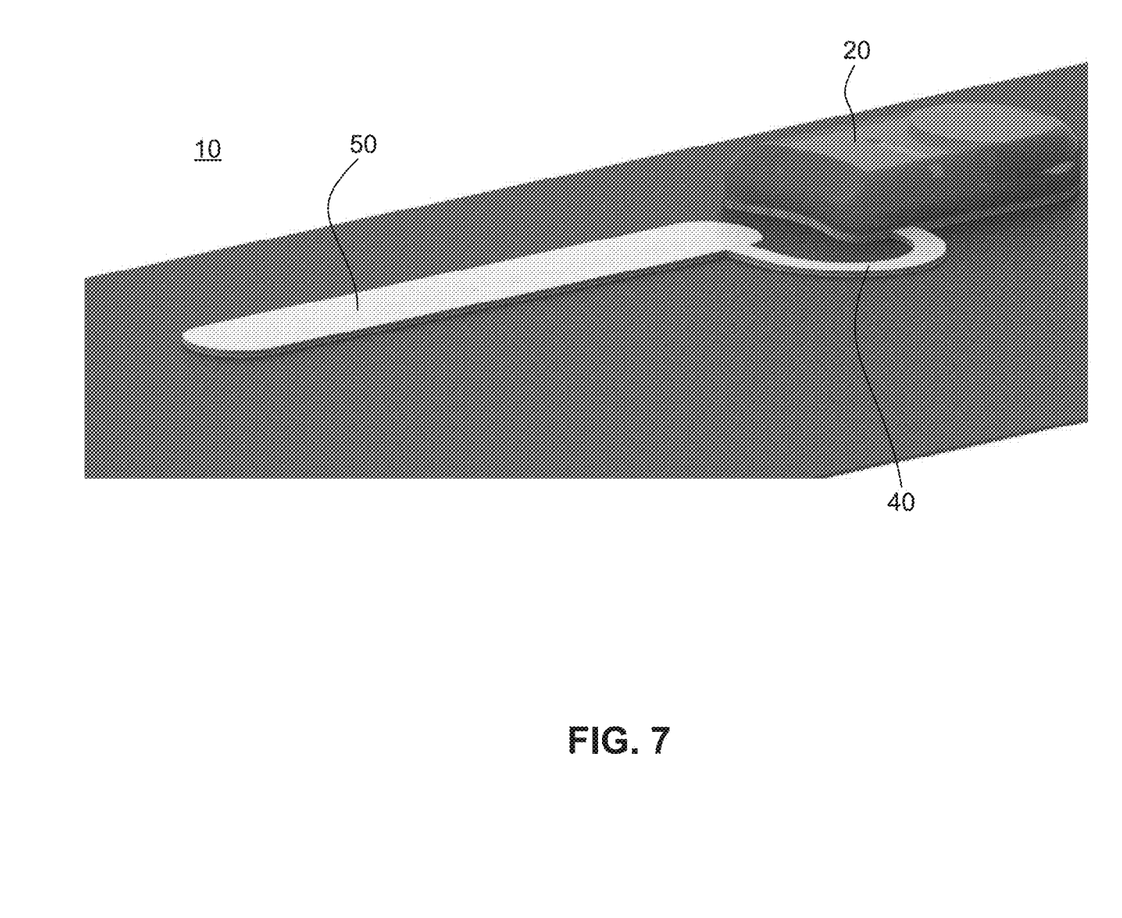
FIG. 7 is an illustration of a capacitive sensor system with an electronic module according to embodiments of the present invention.

With additional technical advantages described with respect to a layered configuration, an additional strain relief innovation is described, along with further aesthetic developments, beginning with FIG. 7. In FIG. 7, a sensor system is shown, which in some embodiments includes a stretchable sensor 50 (e.g., a stretchable capacitive sensor as disclosed above), an electronics module 20 in a housing coupled to the sensor 50, and a strain relief member 40 extending from the stretchable sensor and coupling to the electronics module. In some embodiments, module 20 may be encapsulated in a substrate, or in a film layer such as the film layer described above. In this regard, module 20 may be configured to be used without ports or jacks on the outer surface of the module. When integrated with a garment, for example, module 20 may be wholly encapsulated in a fabric, such that it is hidden from view. In some embodiments, strain relief member 40 extends off axis to the stretching direction of sensor 50. In this regard, strain relief member 40 may be configured such that sensor 50 does not respond to movement of the strain relief member 40. As shown, the connections to the strain relief member 40 and the electronics module 20 (or connections to the strain relief member 40 and sensor 50) are positioned such that the trace is allowed to bend/buckle out of plane relative to the general plane of the electronics module 20 or sensor 50, thereby increasing strain relief. In some embodiments, this avoids formation of fissures or cracks due to material fatigue from either strain cycling or large stress magnitudes.

Figure 8:
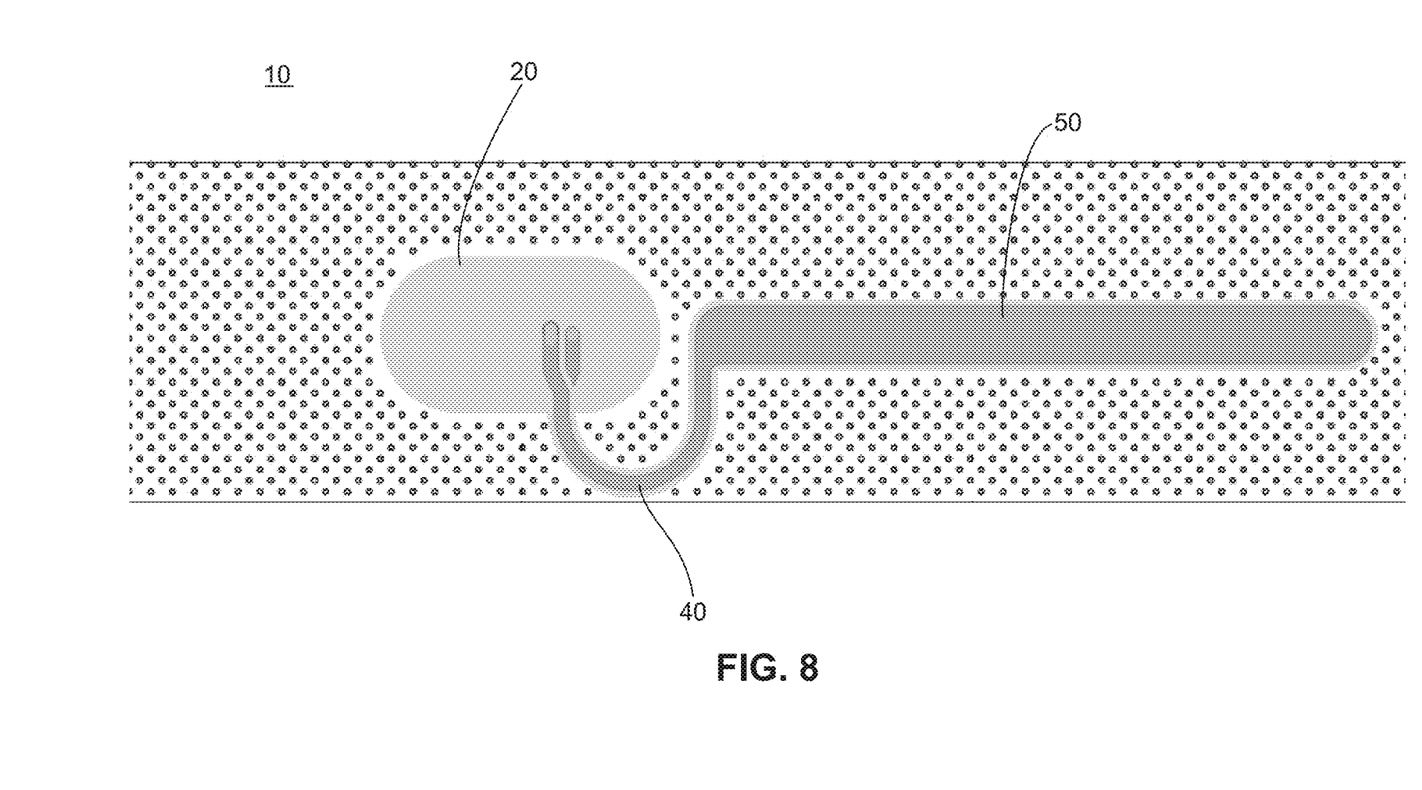
FIG. 8 illustration of a capacitive sensor system with an electronic module according to embodiments of the present invention.

Turning to FIG. 8, an top view embodiment of a sensor system is shown similar to FIG. 7, which in some embodiments includes a stretchable sensor 50 (e.g., a stretchable capacitive sensor as disclosed above), an electronics module 20 in a housing coupled to the sensor 50, and a strain relief member 40 extending from the stretchable sensor and coupling to the electronics module. In some embodiments, as shown in FIG. 8, strain relief member 40 may extend substantially perpendicularly to a longitudinal direction from stretchable sensor 50 (e.g., direction the sensor is designed to stretch and thus measure strain) at the location it couples to the electronics module. In some embodiments, the film layers (as described above) may include a cutout pattern, such that the coupling connection from the sensor 50, strain relief member 40, and electronics module 20 are flush with each other, such that the sensor components lay flat. In this regard, conductive adhesive portions (used in connections 706, for example) may be applied with even pressure.

Advantageously, as opposed to smart phone or smart watch systems, integrated garment sensor systems such as the sensor 50 coupled with module 20 may give individuals freedom to be mindful of their performance without additional distractions. In some embodiments, data may be captured and uploaded and reviewed later, after an activity, which may aid in the individual staying mindful throughout their activity. Also, when coupled with a haptic module, gentle haptic feedback may be given to the individual during the activity, without the need for viewing a screen, or listening for audio feedback, for example. Additionally, being able to focus generally on the activity at hand, rather than raising an arm or looking down, avoids introducing inefficient body positioning or form into the athletic activity. In some embodiments, the sensor may function as an actuator, or input device, sending signals to module 20 when particular contact is detected.

In some embodiments, the breath sensor module 10 is used to detect changes in an individual's direction of motion. Sensor module 10 according to the present invention can also be worn by individuals and used to detect and/or track other motions such as, for example, motions associated with push-ups, pull-ups, weightlifting, diving, gymnastics, et cetera.

By using the sensor module 10 described above, embodiments of the present invention may advantageously enable the individual 1 to obtain timely feedback during an activity about the motion of the individual's 1 body.

While various embodiments of the present invention are described in the general context of yoga, the present invention is not so limited and may be applied in a variety of different sports or athletic activities including, for example, running, sports of soccer (i.e., football), basketball baseball, bowling, boxing, cricket, cycling, football (i.e., American football), golf, hockey, lacrosse, rowing, rugby, running, skateboarding, skiing, surfing, swimming, table tennis, tennis, or volleyball, or during training sessions related thereto.

Various aspects of the present invention, or any parts or functions thereof, may be implemented using hardware, software, firmware, tangible non-transitory computer readable or computer usable storage media having instructions stored thereon, or a combination thereof and may be implemented in one or more computer systems or other processing systems. As discussed, program products, methods, and systems for providing training services of the present invention can include any software application executed by one or more electronic devices device having at least one processor and memory. Embodiments of the present invention may be software executed by a processor, firmware, hardware or any combination thereof in a computing device.

References to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "invention" or "present invention" as used herein is a non-limiting term and is not intended to refer to any single embodiment of the particular invention but encompasses all possible embodiments as described in the application.

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The description of the specific embodiments of the system described with reference to the figures will so fully reveal the general nature of the invention that others can, by applying knowledge within the skill of the art, readily modify and/or adapt for various applications such specific embodiments, without undue experimentation, without departing from the general concept of the present invention.

While various embodiments of the present invention have been described above, they have been presented by way of example only, and not limitation. It should be apparent that adaptations and modifications are intended to be within the meaning and range of equivalents of the disclosed embodiments, based on the teaching and guidance presented herein. It therefore will be apparent to one skilled in the art that various changes in form and detail can be made to the embodiments disclosed herein without departing from the spirit and scope of the present invention. The elements of the embodiments presented above are not necessarily mutually exclusive, but may be interchanged to meet various needs as would be appreciated by one of skill in the art.

It is to be understood that the phraseology or terminology used herein is for the purpose of description and not of limitation. The breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

Further details of the noted systems and methods are set forth in co-pending U.S. application Ser. No. 15/862,138, filed concurrently herewith, which is incorporated by reference herein in its entirety for all purposes.

The invention claimed is:

1. A garment, comprising:
 a breath sensor comprising:
  a stretchable sensor configured to respond to at least one of expansion and contraction of a torso of an individual wearing the garment; and
  electronics comprising:
   a processor; and
   a haptic feedback device,
  wherein in response to the processor determining that the individual's breathing meets predetermined criteria based on the response of the stretchable sensor and without exchanging data with any external device, the processor is configured to automatically direct the haptic feedback device to produce haptic feedback such that the individual is reminded to breathe,
wherein the breath sensor does not include a transmitter or a receiver, and
wherein the breath sensor is completely local and operates without communication with any external device.

2. The garment of claim 1, wherein the predetermined criteria consists of a determination that the individual has not taken a breath within a pre-defined time threshold.

3. The garment of claim 1, wherein the predetermined criteria consists of a determination that the individual is not breathing in a predefined pattern.

4. The garment of claim 1, wherein the haptic feedback is a vibration pattern.

5. The garment of claim 1, wherein the electronics are separable.

6. The garment of claim 1, wherein the electronics include a switch operable by the individual to begin monitoring with the stretchable sensor.

7. The garment of claim 1, wherein the stretchable sensor is a capacitive sensor, comprising:
  a stretchable substrate;
  a first conductor assembly disposed on the substrate; and
  a second conductor assembly positioned above the first conductor assembly such that the second conductor assembly overlaps the first conductor assembly.

8. The garment of claim 1, wherein a connection between the stretchable sensor and the electronics includes a strain relief member configured to isolate the stretchable sensor such that the stretchable sensor measures only stretching of the sensor in a direction configured to measure the breathing of the individual.

9. The garment of claim 1, wherein the breath sensor does not include an audible output or visual output configured to provide feedback to remind the individual to breathe.

10. The garment of claim 1, wherein the garment further comprises:
  a band of elastic material configured to encircle the torso of the individual when the garment is worn by the individual, wherein the stretchable sensor extends longitudinally along the band.

11. The garment of claim 1, wherein the electronics are encapsulated in a fabric of the garment such that the electronics are not visible from an exterior of the garment when the individual is wearing the garment.

12. A method for providing feedback about respiratory activity to an individual wearing a garment comprising a breath sensor having a stretchable sensor configured to respond to at least one of expansion and contraction of a torso of the individual wearing the garment and electronics having a processor and a haptic feedback device, the method comprising:
  sensing a respiratory event via the stretchable sensor, the respiratory event being at least one of the expansion and the contraction of the torso indicating a start of monitoring of the individual's respiratory activity;
  monitoring the individual's respiratory activity via the stretchable sensor and without exchanging data with any external device;
  determining, automatically via the processor and without exchanging data with any external device, that the individual's breathing meets predetermined criteria based on the monitoring; and
  in response to automatically determining that the individual's breathing meets the predetermined criteria, providing immediate feedback from the haptic feedback device to the user,
  wherein the breath sensor does not include a transmitter or a receiver, and
  wherein the breath sensor is completely local and operates without communication with any external device.

13. The method of claim 12, wherein the predetermined criteria consists of a determination that the individual has not taken a breath within a pre-defined time threshold.

14. The method of claim 12, wherein the event sensed comprises one of a user input, determining that the user is breathing, and detection of the garment being worn.

15. The method of claim 12, wherein the immediate feedback is haptic feedback in the form of a vibration pattern.

16. The method of claim 12, further comprising:
  receiving a user input indicating a finish of monitoring of the individual's respiratory activity, wherein the electronics are separable.

17. The method of claim 12, wherein the garment comprises an athletic bra, and wherein the electronics are encapsulated in a fabric of the garment such that the electronics are not visible from an exterior of the garment when the individual is wearing the garment.

18. A respiration monitoring system comprising:
  a garment configured to be worn by an individual;
  a stretchable sensor attached to the garment and configured to respond to at least one of expansion and contraction of a torso of the individual wearing the garment;
  a processor operatively coupled to the stretchable sensor; and
  a haptic feedback device operatively coupled to the processor,
  wherein the stretchable sensor is configured to transmit a non-transitory respiration activity signal to the processor without exchanging data with any device external to the respiration monitoring system,
  wherein in response to the non-transitory respiration activity signal the processor determines without exchanging data with any device external to the respiration monitoring system that a predetermined criteria is met,
  wherein in response to determining that the predetermined criteria is met, the processor causes the haptic feedback device to provide immediate haptic feedback to the individual wearing the garment, and
  wherein the stretchable sensor, processor, and haptic feedback device together are completely local and operate together without communication with any external device, transmitter, or receiver.

19. The respiration monitoring system of claim 18, wherein the stretchable sensor is wirelessly coupled to the processor.

20. The respiration monitoring system of claim 18, wherein the processor is wirelessly coupled to the haptic feedback device.

* * * * *